United States Patent
Verhoeckx et al.

(10) Patent No.: US 9,962,693 B2
(45) Date of Patent: May 8, 2018

(54) FLUIDIC SYSTEM WITH FLUIDIC STOP

(71) Applicant: KONINKLIJKE PHILIPS N.V., Eindhoven (NL)

(72) Inventors: Godefridus Johannes Verhoeckx, Eindhoven (NL); Nicole Henrica Maria Smulders, Eindhoven (NL); Toon Hendrik Evers, Eindhoven (NL); Monica Scholten, Goirle (NL); Menno Willem Jose Prins, Rosmalen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 156 days.

(21) Appl. No.: 14/651,880

(22) PCT Filed: Nov. 18, 2013

(86) PCT No.: PCT/IB2013/060217
§ 371 (c)(1),
(2) Date: Jun. 12, 2015

(87) PCT Pub. No.: WO2014/091334
PCT Pub. Date: Jun. 19, 2014

(65) Prior Publication Data
US 2015/0314283 A1 Nov. 5, 2015

Related U.S. Application Data

(60) Provisional application No. 61/736,612, filed on Dec. 13, 2012.

(51) Int. Cl.
*B01L 3/00* (2006.01)
*F16K 99/00* (2006.01)
(Continued)

(52) U.S. Cl.
CPC ........... *B01L 3/502* (2013.01); *B01L 3/50273* (2013.01); *B01L 3/502738* (2013.01);
(Continued)

(58) Field of Classification Search
CPC ..... B01L 2400/0481; B01L 2300/0816; B01L 3/50273; B01L 3/502738;
(Continued)

(56) References Cited

U.S. PATENT DOCUMENTS 5,627,041 A 5/1997 Shartle
6,296,020 B1 10/2001 McNeely
(Continued)

FOREIGN PATENT DOCUMENTS

JP 2008064748 A 3/2008
WO 0189695 A2 11/2001
(Continued)

*Primary Examiner* — Jennifer Wecker

(57) ABSTRACT

An embodiment of the invention relates to a fluidic system (200) in which a first channel (210) and a second channel (230) are separated by a fluidic stop (220), for example a region with a hydrophobic coating and/or a structure (220) with non-capillary internal dimensions. Moreover, it comprises a flexible element (240) that is deformable to enable a flow of a medium across the fluidic stop.

17 Claims, 6 Drawing Sheets

(51) Int. Cl.
*G01N 1/28* (2006.01)
*B01L 9/00* (2006.01)
*B01J 19/00* (2006.01)

(52) U.S. Cl.
CPC .......... *B01L 9/527* (2013.01); *F16K 99/0017* (2013.01); *F16K 99/0021* (2013.01); *G01N 1/28* (2013.01); *B01L 3/502715* (2013.01); *B01L 3/502723* (2013.01); *B01L 3/502753* (2013.01); *B01L 3/502761* (2013.01); *B01L 3/502776* (2013.01); *B01L 2200/025* (2013.01); *B01L 2200/027* (2013.01); *B01L 2200/06* (2013.01); *B01L 2200/0605* (2013.01); *B01L 2200/0636* (2013.01); *B01L 2200/0647* (2013.01); *B01L 2200/0689* (2013.01); *B01L 2200/10* (2013.01); *B01L 2300/0681* (2013.01); *B01L 2300/087* (2013.01); *B01L 2300/0816* (2013.01); *B01L 2300/123* (2013.01); *B01L 2400/0406* (2013.01); *B01L 2400/0478* (2013.01); *B01L 2400/0481* (2013.01); *B01L 2400/0487* (2013.01); *B01L 2400/0633* (2013.01); *B01L 2400/0655* (2013.01); *B01L 2400/0683* (2013.01); *B01L 2400/0688* (2013.01); *F16K 2099/0084* (2013.01); *Y10T 436/2575* (2015.01)

(58) Field of Classification Search
CPC ....... B01L 2400/0688; B01L 3/502707; B01L 2300/0864; B01L 2300/0867; B01L 2300/087; B01L 2400/0406; B01L 2400/0487
See application file for complete search history.

(56) References Cited

U.S. PATENT DOCUMENTS

| | | | |
|---|---|---|---|
| 7,607,641 B1* | 10/2009 | Yuan | F16K 7/126 137/597 |
| 2002/0114738 A1 | 8/2002 | Wyzgol et al. | |
| 2004/0265172 A1 | 12/2004 | Pugia et al. | |
| 2006/0076068 A1* | 4/2006 | Young | B01F 5/0683 137/829 |
| 2007/0031283 A1* | 2/2007 | Davis | A61B 5/14546 422/400 |
| 2007/0286739 A1 | 12/2007 | Hsieh et al. | |
| 2009/0227041 A1* | 9/2009 | Wang | G01N 35/00069 436/180 |
| 2010/0112723 A1* | 5/2010 | Battrell | G01N 33/53 436/501 |
| 2010/0126927 A1* | 5/2010 | Blankenstein | B01L 3/502707 210/418 |
| 2011/0120580 A1 | 5/2011 | Takahashi | |
| 2011/0301047 A1 | 12/2011 | Immink et al. | |
| 2012/0190128 A1* | 7/2012 | Nikbakht | G01N 1/38 436/180 |
| 2012/0214254 A1 | 8/2012 | Schmidt et al. | |
| 2013/0121893 A1* | 5/2013 | Delamarche | F16K 99/0026 422/503 |

FOREIGN PATENT DOCUMENTS

| | | |
|---|---|---|
| WO | 2008083446 A1 | 7/2008 |
| WO | 2009146160 A1 | 12/2009 |

\* cited by examiner

FLUIDIC SYSTEM WITH FLUIDIC STOP

CROSS-REFERENCE TO PRIOR APPLICATIONS

This application is the U.S. National Phase application under 35 U.S.C. § 371 of International Application No. PCT/IB2013/060217, filed on Nov. 18, 2013, which claims the benefit of U.S. Provisional Patent Application No. 61/736,612, filed on Dec. 13, 2012. These applications are hereby incorporated by reference herein.

FIELD OF THE INVENTION

The invention relates to a fluidic system for transporting a medium, to an apparatus for using such a fluidic system, and to a method for the control of the flow of a medium across a fluidic stop.

BACKGROUND OF THE INVENTION

The U.S. Pat. No. 5,627,041 A1 discloses a cartridge for the analysis of a biological sample, said cartridge comprising a channel with a "stop junction" at which capillary flow of a fluid comes to a rest until a pressure, force, or acceleration is applied to the fluid to overcome said stop junction.

SUMMARY OF THE INVENTION

It would be advantageous to have means that allow for an alternative, robust control of fluid flow, particularly in a fluidic system.

This concern is addressed by a fluidic system according to the present teachings, which further comprise a processing apparatus, a method, and a use.

According to a first aspect, an embodiment of the invention relates to a fluidic system, wherein the term "fluidic system" shall denote a device comprising connected cavities like channels, chambers, inlets, outlets and the like through which a medium can be transported. The medium may particularly be a fluid, for example a liquid of biological origin (blood, saliva, urine etc.). Moreover, the system is preferably a "microfluidic" system in the sense that the characteristic or mean diameter of its cavities (measured e.g. as the diameter of the maximal sphere that fits totally into a cavity) is typically less than about 1000 µm.

The proposed fluidic system comprises a first channel and a second channel that are connected via a fluidic stop. Moreover, it comprises a flexible element having an inner surface arranged such that a determined mechanical pressure applied on an outer surface of the flexible element leads to a local deformation of the inner surface in such a way that a flow of the medium to be transported across the fluidic stop is enabled.

As usual, the term "channel" shall denote a cavity (of arbitrary geometry) through which a medium can be transported. Typically, such a channel has an elongated geometry with a rectangular, circular or polygonal cross section.

A "fluidic stop" shall be any element, unit, structure, or device by which the flow or transport of a medium is impeded, preferably interrupted, under conditions (e.g. pressure in the medium) at which said medium is transported through the adjacent channel(s). A medium introduced into the first channel of the above fluidic system will therefore flow along this channel until it reaches the fluidic stop, where said flow comes to a rest.

The application of a "pressure" on the outer surface of the flexible element is, in the context of the present application, equivalent to the application of a corresponding force. Mentioning of a "determined" pressure refers to the fact that the applied pressure will usually have to fall into a certain range or interval in order to induce the desired effects (i.e. enabling fluid flow).

In general, the roles of the "first" channel and the "second" channel are exchangeable (symmetric). In the following, the channel that is first filled with the transported medium during an application will typically be considered as the "first channel", while the channel into which the medium enters only after passing the fluidic stop is considered as the "second channel".

The described fluidic system has the advantage that it allows for a reliable and robust control of the flow of a medium because said flow is interrupted at a fluidic stop until a significant external measure is taken, namely the deformation of the flexible element. Advantageous is also that the pressure within the medium needs not to be affected to overcome the fluidic stop.

In general, the flexible element may be a part or component of its own. It is then preferably disposed adjacent to the first channel, the second channel, and/or the fluidic stop. In some embodiments, the flexible element may be or comprise a part of the first channel, the second channel and/or the fluidic stop.

The deformation of the inner surface of the flexible element may be permanent (if the range of plastic deformation of the material is reached). Preferably, said deformation is however elastic, thus allowing for a return of the deformed element into its initial state or geometry once the pressure or force causing the deformation is removed.

In general, enablement of a flow across the fluidic stop may be achieved by various mechanisms related to the deformation of the flexible element. The fluidic stop may for example be moved away from the first and the second channel, thus removing a prohibiting influence on the flow of the medium.

In a preferred embodiment, the deformation of the inner surface of the flexible element changes the distance between said inner surface and an opposing element. The "opposing element" may for instance just be or comprise a surface of the first channel, the second channel, and/or the fluidic stop. Moreover, the distance between the inner surface and the opposing element is preferably reduced during deformation of the inner surface. For example, in a system in which the fluidic stop is hydrophilic, having a lower hydrophilicity than the adjacent first channel, and in which the first channel can be deformed to approach the second channel, an aqueous medium will go beyond the fluidic stop because the reduction of the gap between the channels gives an increase of capillary suction.

Optionally, the aforementioned reduction of distance is a reduction to the value of zero, i.e. until the inner surface of the flexible element and the opposing element contact each other. The gap between these elements is then bridged, allowing for a passing over of medium. For example, if the mechanical deformation of the inner surface of the flexible element causes a hydrophilic surface to touch the fluid meniscus of an aqueous medium, the medium will go beyond the fluidic stop because the touching gives an increase of capillary suction.

In another embodiment, the deformation of the inner surface of the flexible element may increase a distance within a cavity or channel. For example, in a system in which the fluidic stop is hydrophobic, an aqueous medium will go beyond the fluidic stop because the increase of gap gives a reduction of the fluid pressure that the fluidic stop can withstand.

In a further development of the fluidic system in which the distance between the inner surface of the flexible element and an opposing element is changed by deformation of the flexible element, a protrusion may be provided on said inner surface of the flexible element and/or on said opposing element. Such a protrusion will contact the meniscus of a medium that is present on the opposite side and constitute a well defined bridge for its continued flow.

In a preferred embodiment, the aforementioned protrusion may have a capillarity and/or a wettability for the medium to be transported in the fluidic system. A medium contacting the protrusion will then readily be taken up and forwarded by said protrusion. A (high) capillarity of the protrusion may be achieved by providing it with a structured surface, comprising for example capillary grooves. A (high) wettability of the protrusion may be achieved by providing it with a suitable surface chemistry with respect to the medium to be transported.

The first and/or the second channel may particularly be designed to allow for the transport of the medium by capillary forces. Depending on the type of medium to be transported, the interior geometry (cross section, length) and the surface chemistry (hydrophilicity) of the channels are chosen appropriately to allow for the generation of capillary forces on the medium. Transportation of the medium will then occur automatically driven by said forces.

Most preferably, the region of the first channel and/or the second channel adjacent to the fluidic stop has a particularly high capillarity for the medium to be transported. Thus it can be guaranteed that the medium will be present in said region when the deformation of the flexible element occurs. If the region of high capillarity is behind the fluidic stop (e.g. in the second channel), the high capillarity has the advantage of readily capturing the medium during and after the deformation.

The feature of interrupting the flow of the medium can be provided to the fluidic stop by various measures. In one embodiment, the fluidic stop may for example contain materials with a lower wettability (or hydrophilicity, if a hydrophilic medium shall be transported) than the adjacent first channel and/or second channel.

In another embodiment, the fluidic stop may be or comprise a component that is repellant for the medium to be transported. If the medium is for example an aqueous liquid, the fluidic stop may be or the fluidic stop may contain a material with hydrophobic properties, e.g. an appropriate surface coating of the fluidic stop.

According to another embodiment, the fluidic stop may have a lower capillarity due to geometrical dimensions, e.g. the fluidic stop has larger interior dimensions than the adjacent first channel and/or second channel. For an arbitrary geometry, the "interior dimension" of a channel or of the fluidic stop may be defined as the diameter of the largest sphere that completely fits into said channel or fluidic stop.

According to another embodiment, the fluidic stop may contain geometrical structures that cause pinning of the fluid meniscus or hindered movement of the fluid meniscus, e.g. a structure with a high curvature such as an edge or a ridge or a roughness.

The flexible element may particularly be or comprise a deformable wall. Hence no joints, hinges or something like that are needed to allow for a movement of two connected parts. Instead, the interior elasticity and/or plasticity of the material constituting the flexible element is exploited to achieve the desired deformation. Most preferably, the wall can be deformed elastically to a degree that allows for a contact with an opposite wall or structure.

The first channel, the second channel, and/or the fluidic stop may optionally comprise a filter element for filtering the medium that is transported. Preferably, such a filter element is located in the channel which is first filled by the medium (e.g. the first channel). This has the advantage that the time during which the flow of the medium is interrupted by the fluidic stop can be exploited for the filtering process and that only filtered medium will have to cross the fluidic stop.

The fluidic system may in general be integrated into any device, apparatus or component in which its properties are needed. In particular, the fluidic system may be incorporated into (or constitute) a cartridge, i.e. into a transportable unit comprising means for the accommodation of a sample medium. The cartridge is typically an exchangeable element or unit with which a sample medium can be provided to an apparatus for processing. It will usually be a disposable component which is used only once for a single sample.

A further embodiment of the invention relates to an apparatus for the processing of a medium, said apparatus comprising the following components:

a) An accommodation space for a fluidic system of the kind described above (i.e. a fluidic system with a first and a second channel that are connected via a fluidic stop, wherein an inner surface of a flexible element is deformable by a pressure on an outer surface of said flexible element for enabling a flow of the medium across the fluidic stop).

b) An actuator for controllably applying a pressure on the outer surface of the flexible element of a fluidic system which is located in the accommodation space.

A fluidic system that can be located in the accommodation space will preferably be (integrated into) a disposable cartridge which is used only once for the processing of a single sample. Moreover, a fluidic system may conceptually be considered as a part of the apparatus, or as a separate component.

The apparatus typically comprises means or components for the desired processing of the medium which is provided in a fluidic system located in the accommodation space. This processing may comprise any manipulation of the medium, for example a physical and/or chemical reaction with the medium. Most preferably, the processing comprises a detection procedure in which properties like the presence and/or amount of certain target substances are determined. A processing apparatus of this kind is for example disclosed in the WO 2010/070521 A1 (which is incorporated into the present application by reference).

A further embodiment of the invention relates to a method for the control of the flow of a medium across a fluidic stop between a first channel and a second channel in a fluidic system, particularly in a fluidic system of the kind described above. The method comprises the deformation of a flexible element to enable a flow of the medium across the fluidic stop.

The method, the fluidic system, and the apparatus are different realizations of the same inventive concept, i.e. the controlled advancement of a medium across a fluidic stop by the deformation of a flexible element. Explanations and definitions provided for one of these realizations are therefore valid for the other realizations, too.

The invention further relates to the use of a cartridge or an apparatus of the kind described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

Simple and high-quality sample taking and processing is important for rapid biosensing applications, in order to guarantee a reliable result even in circumstances with little control, e.g. outside a laboratory and with non-professional users. Preferably a reliable measurement is done on only a small sample volume, and the sample taking should not generate pain. Methods to get a small fluid sample comprise for example a pin prick, a needle, a capillary etc. For biosensing applications, it is important to view the sample taking in combination with the subsequent processing, i.e. the cartridge and reader technology (assuming that the sample is handled in a cartridge). An example of a technology for rapid biosensing is the Magnotech® technology developed by the applicant. The fluidic systems and cartridges that will be described in the following may (inter alia) be used with this biosensing technology.

Disposable cartridges for the analysis of for example components in body fluids, such as blood, urine, saliva, are often based on the mechanism of capillary flow. For certain use cases it is advantageous to take up the sample into the cartridge, while the cartridge is outside the analyzer. Often the intended assay contains a number of time-critical processes which are carried out under control by the analyzer. This implies that the sample should not wet the assay/detection area before the cartridge is loaded into the analyzer. A solution which is easy-to-use for the end-user can be based on storage of the sample inside the cartridge and release of the sample triggered at the desired moment by the analyzer. Such a solution depends on a valve which is capable of starting capillary flow at the desired moment.

Figure 1:
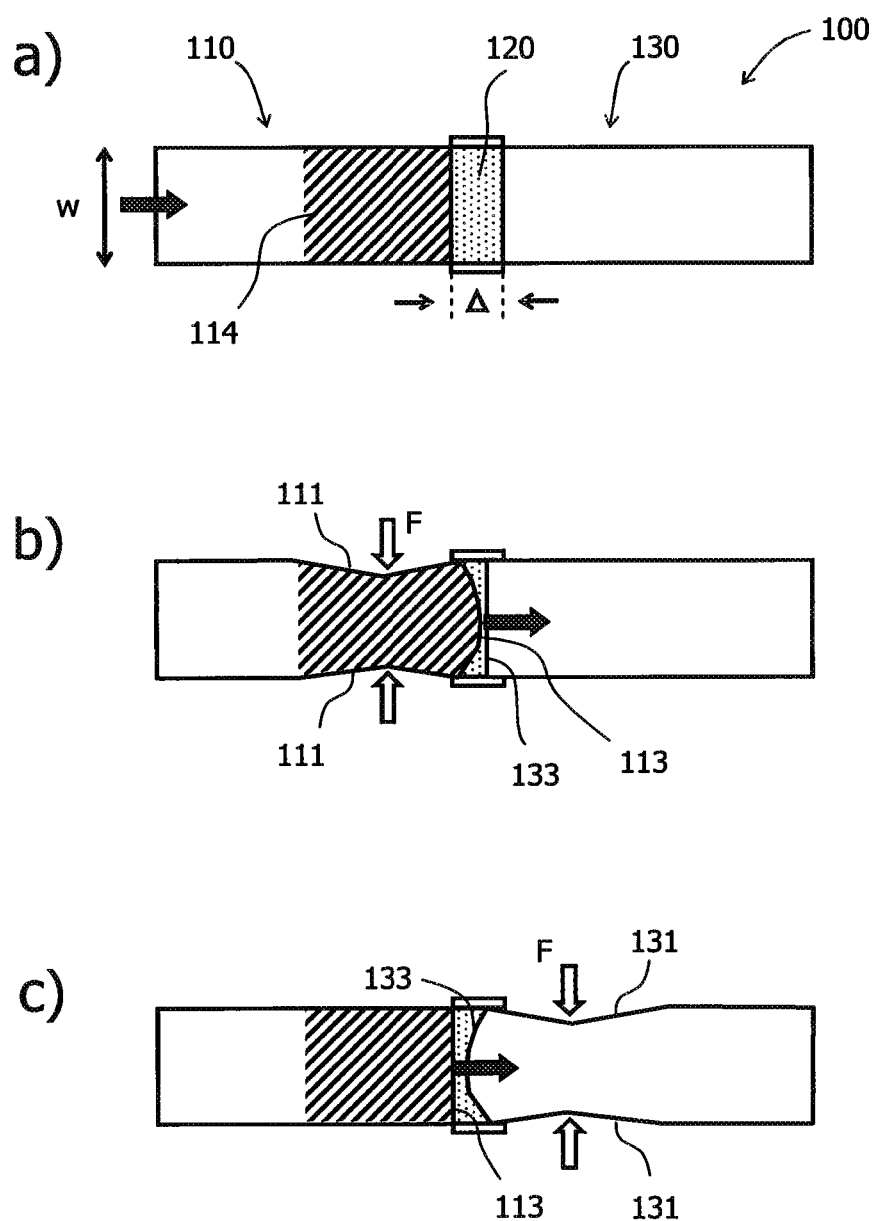
FIG. 1 shows a fluidic system according to a first embodiment of the present invention (a) in an initial resting state with fluid in a first channel, (b) when said first channel is deformed, (c) when a second channel is deformed.

FIG. 1 shows a fluidic system 100 according to a first embodiment of the present invention by which the above issues are addressed. The elements shown in the Figure are typically a part of a larger fluidic system, particularly a fluidic system that is incorporated into a disposable cartridge which can be used to take up a sample medium (e.g. a biological liquid) and to provide it to a reading apparatus. The Figure concentrates on the essential components around a fluidic stop. These components comprise:

- A first channel 110, for example realized as a cavity of width w with a rectangular cross section, which is typically connected on its left side to further components (not shown) for the introduction of a sample medium into said first channel. The first channel optionally comprises a region 114 of increased capillarity (with respect to the medium to be transported) on its right end. Said increased capillarity may for example be achieved by a reduced channel height and/or by a particular surface coating.
- A second channel 130 that is disposed in line with the first channel but separated from it by a gap of width A. The second channel 130 is connected at its right end to further components (not shown) in which a further processing of the transported medium shall take place (e.g. a sample chamber with capture sites for target molecules).
- A fluidic stop 120 that is disposed in the aforementioned gap between the first channel 110 and the second channel 130. The fluidic stop 120 is designed such that it interrupts the flow or transportation of a medium occurring in the first channel 110. This may particularly be achieved by a low capillarity of the fluidic stop, for instance due to larger interior dimensions of the fluidic stop and/or to an appropriate surface coating (e.g. a hydrophobic coating if an aqueous medium shall be transported) and/or due to structures that cause pinning or hindered movement of the meniscus.

As already mentioned, the described fluidic system 100 will typically be incorporated into a cartridge with an inlet portion (not shown) for taking up a sample fluid, said inlet portion being connected to the first channel 110 and allowing for a flow of a sample fluid along said first channel until it reaches the fluidic stop 120. Such a filling state is assumed in FIG. 1a).

In order to allow for a further advancement of the medium into the second channel 130, for example for starting a detection assay in or behind said second channel, it is proposed to overcome the fluidic stop 120 by a deformation of a flexible element located adjacent to said fluidic stop. This flexible element may be a component of its own and/or be a part of the first channel (FIG. 1b), the second channel (FIG. 1c), and/or the fluidic stop (FIGS. 2-15).

FIG. 1b) illustrates a first alternative in which the first channel 110 is deformed by an appropriate pressure or force F acting on its side walls (outer surfaces 111). Due to this force F, the first channel bulges until an inner surface 113 thereof contacts the second channel 130. At this moment, the fluid meniscus is touched and the medium filling the first channel can pass over into the second channel, thus overcoming the fluidic stop 120 and continuing the flow of medium into/through the second channel. The force F may for example be generated manually by a user, or via some intermediate instrument, e.g. as part of the analyzer.

FIG. 1c) illustrates a second alternative in which the second channel 130 is deformed by an appropriate force F acting on its side walls 131. Again, this leads to a contact between the first channel and an inner surface 133 of the second channel, thus enabling a passing over of medium into the second channel.

In general, the part of the fluidic system that touches the medium to be transported will preferred have a good wettability for the fluid medium. Touching for example an aqueous medium against a hydrophilic material will cause wetting and thus a facilitated outflow of the medium.

Figure 2:
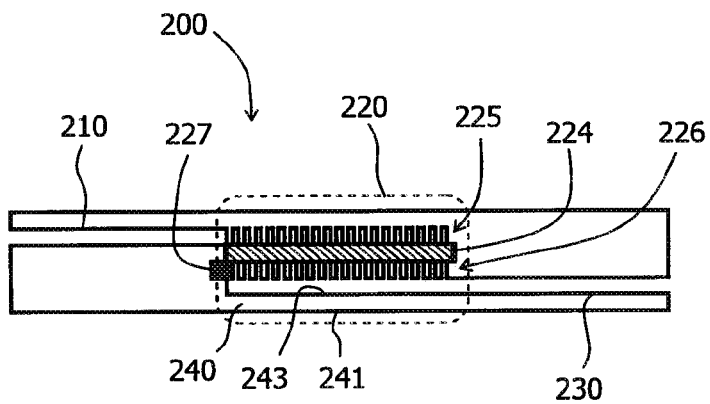
FIG. 2 schematically shows a section through a cartridge with a fluidic system according to a second embodiment of the present invention, said system comprising a filter element and a separate flexible element.

FIG. 2 shows a cartridge 200 constituting a second embodiment of a fluidic system comprising a first channel 210 and a second channel 230 that are separated by a fluidic stop 220. In this case, the fluidic stop contains a structure with multiple channels in parallel, e.g. a comb-like structure and/or a filter element. In this example, a filter element 224 is disposed in the fluidic stop 220, said filter element optionally being held between comb-like support structures 225, 226 with small micro fluidic dimensions. The channels 210, 230 may have hydrophilic surfaces to allow for a transport of a fluid medium by capillary forces. If necessary, edges of the filter element 224 can be blocked with a hydrophobic material 227.

The flow-interruption mechanism of the fluidic stop 220 is realized in this embodiment by an empty gap separating the filter element 224 (and its lower support 226) from an opposite wall 240 and the second channel 230. The aforementioned opposite wall has an inner surface 243 facing the filter element 224 and its support 226 and an outer surface 241. Moreover, it shall be deformable and constitutes in this embodiment the "flexible element" that is used to overcome the fluidic stop.

It should be noted in this context that the assignment of components as belonging to the fluidic stop is to some extent arbitrary. In the above description, the support structures 225 and 226, the filter element 224, and the deformable wall 240 were all considered as belonging to the fluidic stop 220. Alternatively, the fluidic stop could be identified with just the empty gap between the lower support 226 and the deformable wall 240 (in which case the support structures 225, 226 and the filter element 224 would be considered as parts of the first channel, and the deformable wall would be considered as a separate component). Whichever of these or other possible definitions is chosen does however not affect the general concept that is realized by the described embodiments.

If a medium is introduced into the first channel 210, it will advance, driven by capillary forces, until it fills the filter element 224 and the adjacent support 226. The medium will not proceed any further due to the gap between the lower support 226 and the deformable wall 240 in the fluidic stop 220.

For example, if a sample of whole blood is introduced into the first channel 210, the red blood cells will stay in the filter element 224 while the plasma flows into the filter support 226. The filter element 224 and its optional filter support 226 represent areas with high capillary force. As there is no contact with the rest of the (hydrophilic) cartridge, the fluid flow will stop at this stage.

Figure 3:
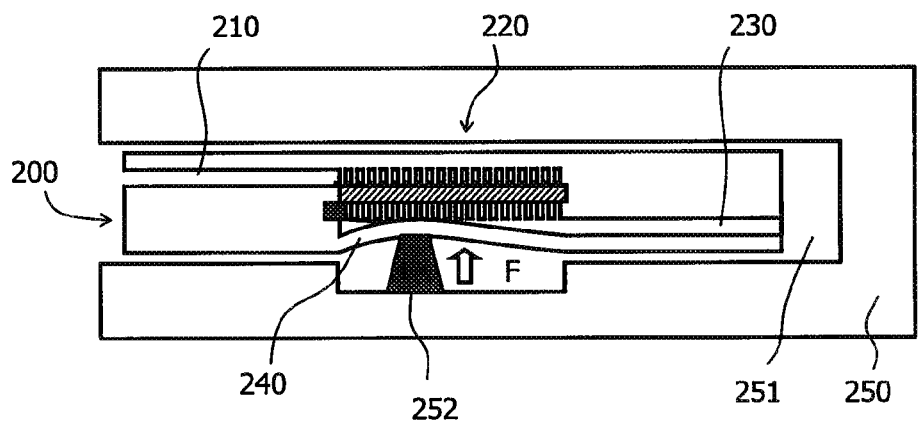
FIG. 3 schematically shows the cartridge of FIG. 2 after introduction into a reading apparatus in which the flexible element is deformed.

FIG. 3 shows the cartridge or fluidic system 200 after its introduction into an apparatus, for example a reading apparatus 250 for the detection of target components (e.g. molecules) in the sample medium provided in the cartridge 200. The cartridge 200 is disposed in an accommodation space 251 of the reading apparatus 250. In this position, a movable actuator 252 of the apparatus 250 contacts the outer surface 241 of the flexible element 240 and deforms it such that its inner surface 243 comes into contact with the opposite support 226 and/or the filter element 224. Accordingly, the fluidic stop is broken and medium (e.g. plasma) can pass over into the second channel 230.

Figure 4:
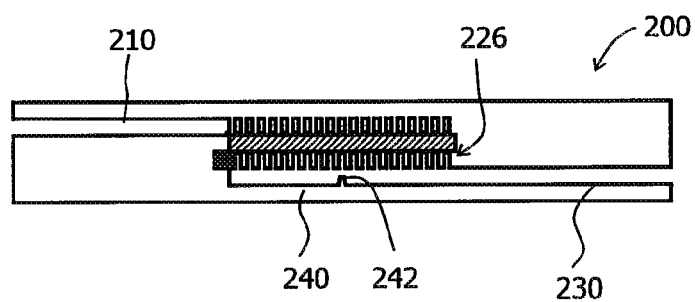
FIG. 4 shows a modification of the cartridge of FIG. 2 in which the flexible element comprises a contact protrusion.

FIG. 4 shows an optional modification of the cartridge 200, in which the inner surface 243 of the flexible element 240 comprises a protrusion 242 facing the support 226 of the filter element 224. Upon deformation of the flexible element 240, this protrusion 242 will early contact the first channel and the medium there, thus minimizing the required deformation of the flexible element.

A principle underlying the described embodiments is that for liquid transport under capillary action a physical contact between the liquid and the surface where it should go to is required. If there is no physical contact between a surface and the liquid a "pulling" capillary force is absent. Due to this requirement it is often difficult to transfer liquid from one layer in a device that is built up of several layers towards another layer.

One example of a device that is built up of several layers is a hybrid device or cartridge in which an injection molded part is combined with a foil or a stack of foils containing micro fluidic structures. In such a hybrid device, one can use the flexibility/deformability of the fluidic structures in the foil section to bring liquid into physical contact with a contact area, particularly with a protrusion (e.g. a pin) on the molded part.

This approach will in the following be described in more detail with respect to embodiments comprising a structure for transferring liquid from one part in a micro fluidic device to an other part in that same device. The structure consists of a protrusion (or pin) integrated on the part where liquid has to go to. The protrusion must physically touch the liquid in a capillary structure on the other (wetted) part to transfer liquid from the wetted part to the part that is still dry.

Figure 5:
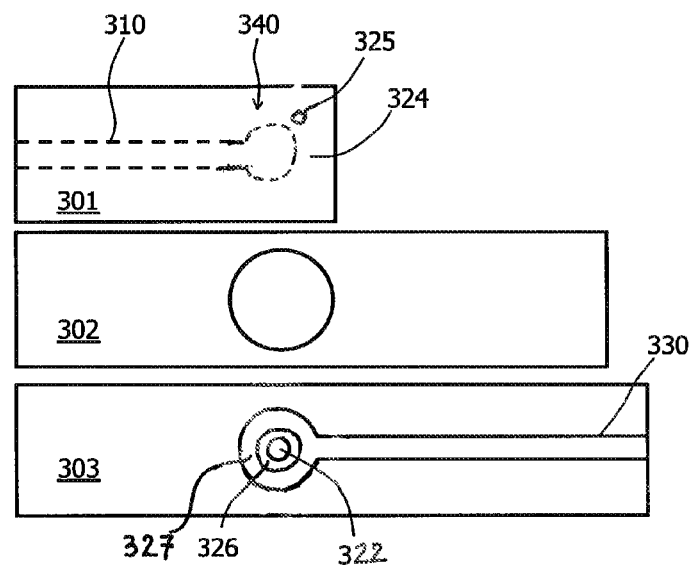
FIG. 5 shows a top view onto three layers of a cartridge according to a third embodiment of the present invention.
Figure 6:
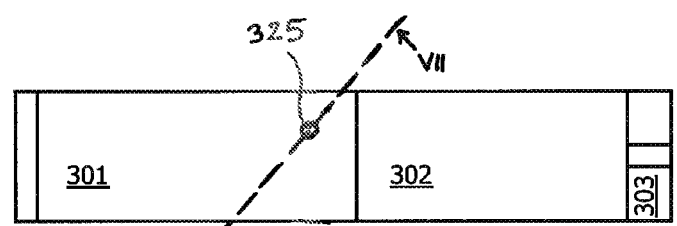
FIG. 6 shows a top view onto the cartridge of FIG. 5 in the assembled state.
Figure 7:
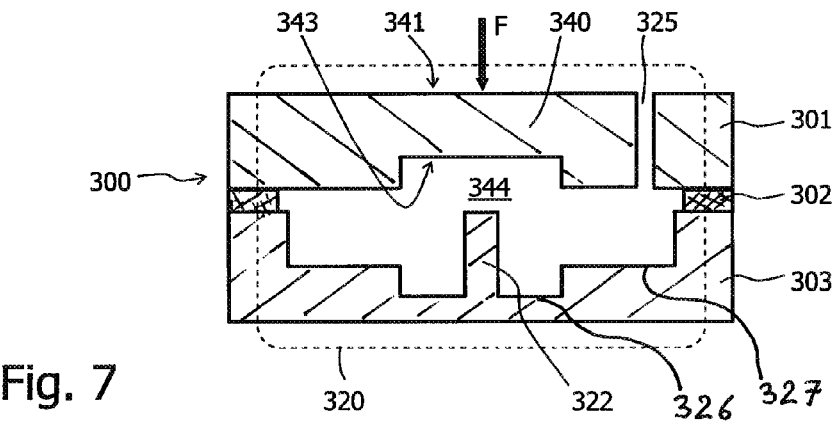
FIG. 7 shows a section along line VII-VII of FIG. 6.
Figure 8:
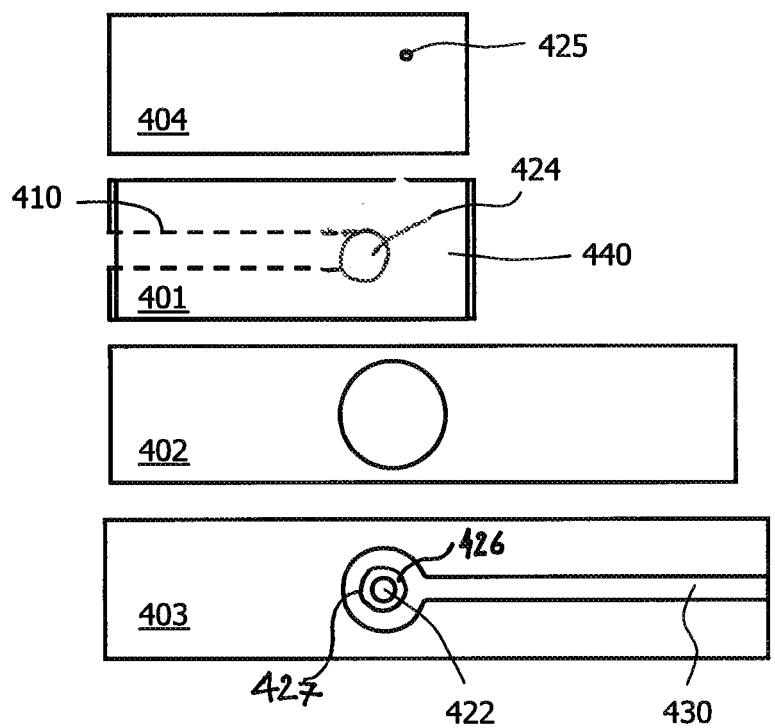
FIG. 8 shows a top view onto four layers of a cartridge according to a fourth embodiment of the present invention.
Figure 9:
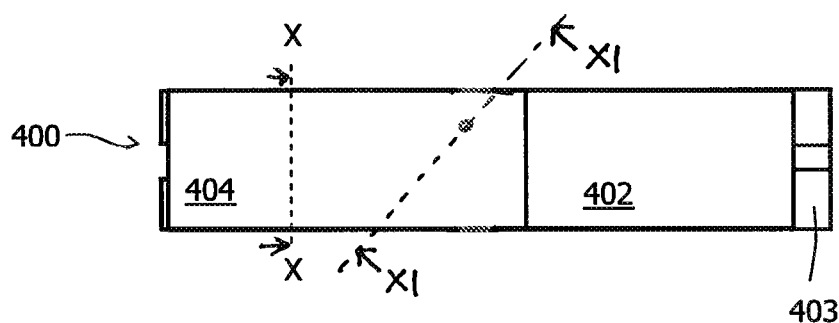
FIG. 9 shows a top view onto the cartridge of FIG. 8 in the assembled state.

FIGS. 5-7 show a fluidic system or cartridge 300 that is designed according to the above principles. The cartridge 300 is a hybrid device comprising, from top to bottom, the following layers:

A top foil 301 with a hot embossed (hydrophilic) first channel 310 leading to an enlarged, circular top section 324 of a pond. Moreover, a small air vent 325 is provided in this foil 301 (this should be disposed in a remote position, otherwise it may be closed by liquid filling the pond).

A joining layer 302 with a circular hole (forming the central section of the mentioned pond). This layer can for example consist of glue or a double sided tape.

An injection molded (plastic) part with a second channel 330, a bottom section 326 of the pond, a (hydrophilic) protrusion or pin 322 and a depression 327. The depression 327 may be useful to accommodate the top foil 301 when it is pressed downward. This is necessary in case that the top of the pin 322 is at the level of or below the top surface of the injection molded part 303. It also prevents part 303 touching the top of the pond 340, with a risk of closing it.

The mentioned layers are shown separately in a top view in FIG. 5. A top view of the assembled cartridge 300 is shown in FIG. 6, while a section across line VII-VII of FIG. 6 is shown in FIG. 7.

As can be seen from FIG. 7, the whole structure around the pond 344 is considered as a fluidic stop 320. Moreover, the top foil 301 (or, more precisely, the region of this foil above the pond 344) constitutes a "flexible element" 340 that can be deformed by application of a force F on its outer surface 341. Upon application of such a force, the foil 301 bends towards the protrusion 322 until the gap between the inner surface 343 of the flexible element 340 and said protrusion becomes zero or at least small enough to enable the passing over of fluid to the protrusion and from there into the second channel 330.

The small hole 325 in the top foil 301 is used to prevent generation of pressure variations caused by compression of the foil. This could lead to unwanted liquid movement in the detection chambers.

FIGS. 8-11 show an alternative embodiment of a cartridge 400. This cartridge has substantially the same design as the cartridge 300, except for the top section 424 of the pond 444 being die-cut into the foil 401 instead of being hot embossed (as is the channel 410). This die-cut hole 424 is covered by a hydrophilic lid 404 with a vent hole 425.

With the described design, the wedges in the top part of the pond 444 can be made sharper, which improves capillary filling of the top of the pond. Also, wetting of the bottom of the pond, in injection molded part 403, can be improved by choosing the proper hydrophilic material. In this way filling of the pond can be achieved easier.

Figure 10:
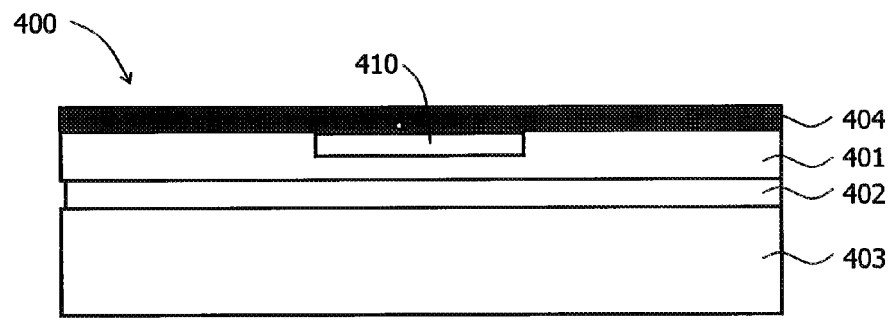
FIG. 10 shows a section along line X-X of FIG. 9.

FIG. 10 shows that the first channel 410 is located at the top side of this foil, i.e. it is separated from the injection molded part 403 by the material of the foil 401.

The microfluidic structure(s) in the foil(s) 301, 401 can be made by any technique capable of creating microfluidic structures in foil, such as roll-to-roll hot embossing, flat bed hot embossing, die cutting or combinations thereof.

Liquid transport via the protrusions 322, 422 of the cartridges 300, 400 can optionally be enhanced by improved wettability of the protrusion (lower contact angle). This can for example be achieved by an appropriate hydrophilicity of the protrusions. Additionally or alternatively, liquid transport via the protrusions can be enhanced by creation of grooves in the protrusion that act as capillary channels.

Figure 11:
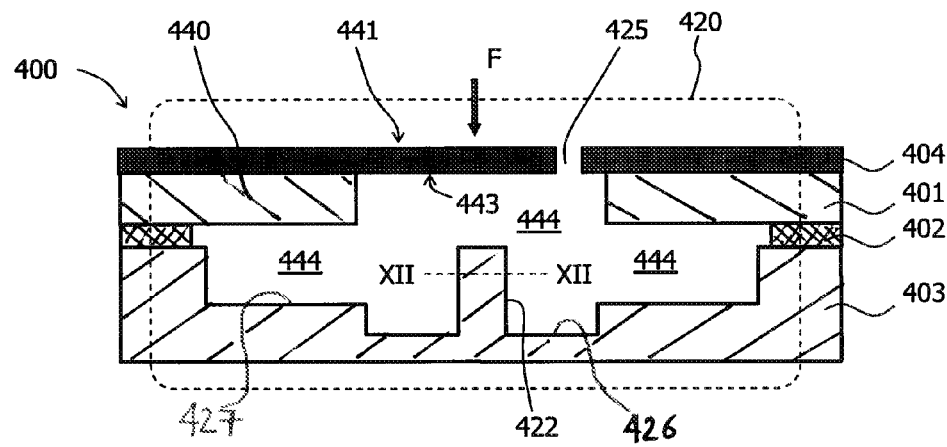
FIG. 11 shows a section along line XI-XI of FIG. 9.
Figure 12:
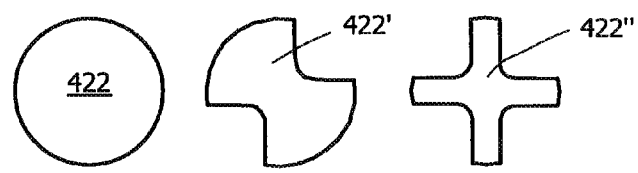
FIG. 12 shows three alternatives for a cross section along line XII-XII of FIG. 11 through a protrusion.

FIG. 12 shows in this respect possible alternative cross sections of the protrusion 422 of FIG. 11. The shown examples comprise the "normal" circular cross section of a protrusion 422, a cross-shaped cross section of a protrusion 422", and cross section of a protrusion 422' with an intermediate shape.

Figure 13:
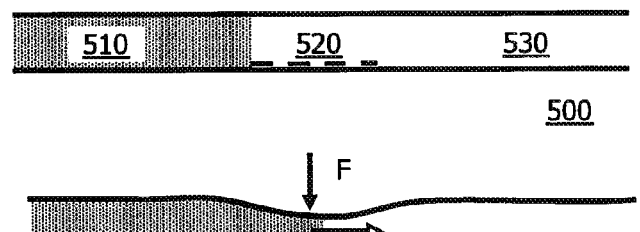
FIG. 13-15 illustrate how a deformation of the fluidic stop can be used to forward the medium.
Figure 14:
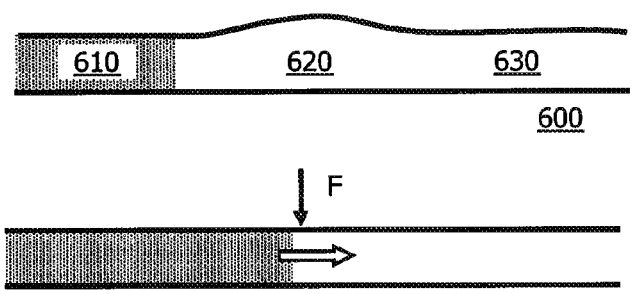
Figure 15:
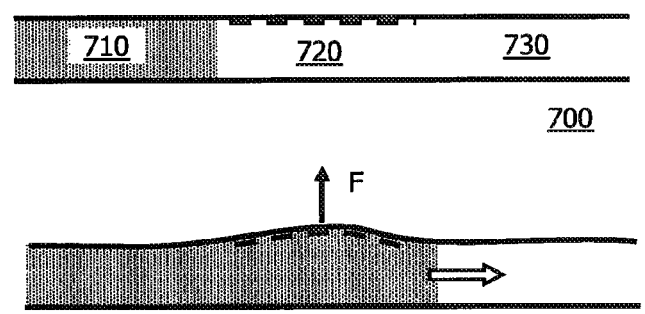

FIGS. 13-15 illustrate three exemplary ways how a deformation of the fluidic stop can be used to overcome said stop. In these embodiments, the fluidic stop (or at least one of its walls) is simultaneously a flexible element that can be deformed by a pressure on an outer surface thereof.

In FIG. 13, the fluidic stop 520 between a first channel 510 and a second channel 530 comprises a region with reduced hydrophilicity (assuming that the medium to be transported is hydrophilic). Deformation of the fluidic stop by a force F reduces the capillary distance and thereby increases the capillary force, enabling the passage of the medium.

In FIG. 14, the fluidic stop 620 between a first channel 610 and a second channel 630 comprises a region with reduced capillarity due to a larger gap between its walls. Deformation of the fluidic stop by a force F reduces the capillary distance and thereby increases the capillary force.

In FIG. 15, the fluidic stop 720 between a first channel 710 and a second channel 730 comprises a region with hydrophobicity (assuming that the medium to be transported is hydrophilic), or a region with geometrical structures that hinder meniscus movement, e.g. by a certain degree of meniscus pinning. Deformation of the fluidic stop by a force F increases the capillary distance and thereby reduces the stopping force.

In a modification of the described embodiments, protrusions could be created on the foil parts, enabling transfer from a foil to a different foil (e.g. in a cartridge made of a stack of foils). Moreover, the main focus in the above sketches was on the valve around the fluidic stop. Typically, the molded and foil parts will contain more fluidic functions than the simple connection of channels which are shown here.

The described fluidic systems maintain the principle of capillary ("passive") filling. Hence there is no need for the application of external pressure to the fluid, which often creates complicated and therefore expensive solutions (e.g. involving air tight rubbers, rotating disks etc.). Furthermore, it may be hard to control pressures/volumes in order to safeguard stopping of liquid at the right positions. In capillary micro fluidics the stopping of liquid is controlled by the fixed geometrical features of the device.

The fluidic stop and the deformable element in the described fluidic systems essentially show a valve action. Optionally, such a valve can be closed again when the deformation is removed by taking away the external actuation. In this way an "open/close" valve is achieved rather than an "open once" valve. A valve of the described type can be applied several times in series in a channel that vents to the same exit (such a cascade of valves would not be possible by opening of one single venting hole).

In summary, the described embodiments show a valve for capillary microfluidic devices. The valve may comprise a protrusion on a second, non-wetted part. When a liquid is present in a channel or structure in a first wetted part, the liquid can flow by capillary forces from the wetted part to the dry part. If the protrusion is slightly too short to cause liquid transfer and the wetted part is a deformable foil, the foil can be deformed by external forces to cause transfer. In this way conditional transfer (valving) is achieved, no external pressure has to be applied on the liquid. The external force can be applied by an analyzer.

The cartridges 200, 300, 400 may be realized as a "fully integrated cartridge" in the sense that a Sample Taking Unit ("STU") and a Detection Assay Unit ("DAU") are integrated in one single piece.

One method to use such a cartridge is that the user puts a sample into the cartridge while it is outside the associated reader apparatus, and then puts the loaded integrated cartridge into said reader. Advantages of this approach are that the user can take the sample without the reader, a freedom to choose the sampling area on the body, a freedom of the patient to move, a freedom of the sampling location being away from the reader location, possibly less stress for the patient (cartridge approaches the patient, the patient is not pulled toward the reader).

Another method to use such a cartridge is that the user puts a sample into the cartridge while the cartridge is inside the reader. Advantages of this approach are that the reader controls and monitors the sampling process and that the cartridge can be fed from a stock in the reader (e.g. a carrousel).

Alternatively, the cartridge 200 may be realized as a cartridge with separate Sample Taking Unit ("STU") and Detection Assay Unit ("DAU").

One method to use such a cartridge is that the user takes a sample into the STU, inserts the DAU into the reader, and clicks the filled STU onto the DAU when it is in the reader.

An advantage of this approach is that the DAU can be fed from a stock in the reader (e.g. a carrousel).

Another method to use such a cartridge is that the user takes the sample into the STU, clicks the filled STU onto the DAU before it is in the reader, and thereafter clicks STU with the DAU into the reader.

In summary, embodiments of a fluidic system have been described in which a first channel and a second channel are separated by a fluidic stop, for example a region with a hydrophobic coating and/or a chamber with non-capillary internal dimensions. At least one of the first channel, the second channel, and the fluidic stop is deformable to enable a flow of a medium across the fluidic stop.

Cartridges according to the described embodiments may comprise a Sample Taking Unit (STU) and a Detection Assay Unit (DAU) with the following preferred features:

The STU contains four functional modules:
a sample entry port or inlet portion (with e.g. needles, foil, skin adhesive);
a sample or assay chamber;
a suction mechanism (e.g. preloaded vacuum, vacuum generation module);
an extraction port (e.g. septum, outlet to DAU).

The STU-DAU interface comprises:
a channel;
optional: a valving mechanism (e.g. capillary stop, permeable viscoelastic medium, releasable mechanical obstruction, gas entrapment in the DAU with vent piercing, diode valve).

The DAU contains:
a sample inlet port;
a channel;
a transport mechanism (e.g. capillary forces, gravity, preloaded vacuum, generated vacuum, mechanical volume displacement pump);
an assay chamber (e.g. magnetic nanoparticles, biosensing surface).

Optional functions that are distributed over the above components are:
a sample filtering;
a reagent storage and release;
a sample adequacy sensor/indicator.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A fluidic system for transporting a medium, comprising:
a first channel;
a second channel;
a flexible element disposed between the first channel and the second channel, and having an inner surface, wherein without application of a force to the flexible element, a gap exists between the first and second channel; and
a fluidic stop that connects the first channel and the second channel disposed between the first channel and the second channel; wherein the flexible element is arranged such that a determined mechanical pressure (F) applied on an outer surface of the flexible element and is configured to produce a local deformation of the inner surface of the flexible element, thereby reducing the gap between the first and second channels and changing a distance ($\Delta$) between the inner surface of the flexible element and the second channel in such a way that a flow of the medium across the fluidic chop is enabled.

2. The fluidic system according to claim 1, wherein the flexible element comprises a part of the first channel, the second channel, and/or the fluidic stop.

3. The fluidic system according to claim 1, wherein the inner surface of the flexible element comprises a protrusion.

4. The fluidic system according to claim 3, wherein the protrusion is wettable by the medium and/or allows for the transporting of the medium by capillary forces.

5. The fluidic system according to claim 1, wherein the first channel and/or the second channel allow for the transporting of the medium by capillary forces.

6. The fluidic system according to claim 5, wherein the fluidic stop has a lower capillarity than the first channel and/or the second channel.

7. The fluidic system according to claim 1, wherein the fluidic stop comprises a medium-repellant component or a geometrical structure for an at least partial pinning of a meniscus.

8. The fluidic system according to claim 1, wherein the fluidic stop has larger interior dimensions than the first channel and/or the second channel.

9. The fluidic system according to claim 1, wherein it comprises multiple channels in parallel and/or a filter element.

10. The fluidic system according to claim 1, characterized that it is incorporated into a cartridge.

11. A processing apparatus, comprising:
an accommodation space for a fluidic system according to claim 1; and
an actuator for controllably applying a pressure (F) on the outer surface of the flexible element of a fluidic system in the accommodation space.

12. A method for control of flow of a medium across a fluidic stop between a first channel and a second channel in a fluidic system, wherein without application of a force to a flexible element, disposed between the first and second channel, the method comprising: deforming the flexible element, the fluidic stop being located between the first and second channel, and by the deforming, reducing the gap between the first and second channel, and changing a distance ($\Delta$) between the inner surface of the flexible element and the second channel in such a way that a flow of the medium across the fluidic chop is enabled.

13. The fluidic system according to claim 1, wherein the fluidic stop comprises multiple channels in parallel and/or a filter element.

14. The fluidic system according to claim 1, wherein a region of increased capillarity is disposed adjacent to the fluidic stop.

15. The fluidic system according to claim 1, further comprising a surface coating wherein the surface coating comprises a hydrophobic coating.

16. The fluidic system according to claim 1, wherein the first channel has a width, a height, and a rectangular cross section, the first channel comprising a region having an increased capillarity compared to a remainder of the first channel, the first channel having a reduced channel height, or a surface coating, or both, to provide the increased capillarity.

17. The fluidic system according to claim 1, wherein the first channel comprises a region having an increased capillarity compared to a remainder of the first channel, the first channel having a reduced channel height, or a surface coating, or both, to provide the increased capillarity.

* * * * *